(12) United States Patent
Yamamoto et al.

(10) Patent No.: US 7,470,753 B2
(45) Date of Patent: Dec. 30, 2008

(54) SILICONE-MODIFIED ANTIMICROBIAL POLYMER, ANTIMICROBIAL AGENT AND ANTIMICROBIAL RESIN COMPOSITION

(75) Inventors: Yuichi Yamamoto, Chiba (JP); Jun Hiraki, Toko (JP)

(73) Assignee: Chisso Corporation, Osaka (JP)

( * ) Notice: Subject to any disclaimer, the term of this patent is extended or adjusted under 35 U.S.C. 154(b) by 843 days.

(21) Appl. No.: 10/840,235

(22) Filed: May 7, 2004

(65) Prior Publication Data
US 2004/0228826 A1 Nov. 18, 2004

(30) Foreign Application Priority Data
May 15, 2003 (JP) ............................. 2003-137031

(51) Int. Cl.
*C08G 77/38* (2006.01)
(52) U.S. Cl. .................. 525/474; 525/476; 525/479
(58) Field of Classification Search ............... 525/476, 525/479, 474
See application file for complete search history.

(56) References Cited

U.S. PATENT DOCUMENTS 4,539,234 A 9/1985 Sakamoto et al.
4,775,585 A 10/1988 Hagiwara et al.
6,358,501 B1 * 3/2002 Dietz et al. ............... 424/70.12
6,398,911 B1 6/2002 Schroeder et al.

FOREIGN PATENT DOCUMENTS

| EP | 0 291 130 | 11/1988 |
|---|---|---|
| JP | 54-147220 | 11/1979 |
| JP | 59-133235 | 7/1984 |

OTHER PUBLICATIONS

Haruyoshi Seino et al., "Usefulness of New Chitosan Derivative Forming Polymer Emulsion as Cosmetic Ingredients", Japan Cosmetic Journal, vol. 26, No. 2, pp. 71-78, 2002.
Munehiko Tanaka, "Modification of Functional Properties of Protamine and Polylysine", Foods Food Ingredients Journal Japan, No. 185, pp. 23-30, 2000.

* cited by examiner

*Primary Examiner*—Kuo-Liang Peng
(74) *Attorney, Agent, or Firm*—Wenderoth, Lind & Ponack, L.L.P.

(57) ABSTRACT

The present invention provides ε-polylysine represented by formula (1), having a polyorganosiloxane group introduced into the molecule, and a process for production of the ε-polylysine, in which the formula (1) is defined in the specification. The invention further provides an antimicrobial agent comprising an amino group-containing antimicrobial polymer having a polyorganosiloxane group introduced into the molecule, and an antimicrobial resin composition comprising an antimicrobial agent above and a resin.

5 Claims, 7 Drawing Sheets

SILICONE-MODIFIED ANTIMICROBIAL POLYMER, ANTIMICROBIAL AGENT AND ANTIMICROBIAL RESIN COMPOSITION

BACKGROUND OF THE INVENTION

1. Field of the Invention

The present invention relates to an antimicrobial polymer having a polyorganosiloxane group introduced into the molecule, to a process for its production, to an antimicrobial agent and to a composition comprising the antimicrobial agent and a resin. More specifically, the invention relates to ε-polylysine having a polyorganosiloxane group introduced into the molecule and a process for its production (the ε-polylysine will hereinafter be referred to as "silicone-modified ε-polylysine"), to an antimicrobial agent comprising an amino group-containing antimicrobial polymer having a polyorganosiloxane group introduced into the molecule (the polymer will hereinafter be referred to as "silicone-modified antimicrobial polymer" and the antimicrobial agent will hereinafter be referred to as "silicone-modified antimicrobial agent"), and to a composition comprising the silicone-modified antimicrobial agent and a resin.

2. Related Art

A large assortment of bacteria and molds exist in human living spaces. Such microbes often produce decomposition of foods and generate malodors, resulting in a discomforting environment. They are also responsible for various diseases including food poisoning and dermopathies such as tinea and the like, and in certain cases can even be life threatening to individuals with weakened resistance, such as infants and the elderly. Since inhibition of microbial proliferation is an important aspect of sanitary and comfortable living, it has become desirable to provide antimicrobial functions for a wide variety of common medical products, subsistence goods and clothing.

Synthetic resins are preferred as materials to be used for medical products, subsistence goods, clothing and the like because they are lightweight, strong and can be freely shaped according to the purpose. Most synthetic resins, however, do not by themselves exhibit antimicrobial functions. It has therefore been common to add various antimicrobial agents to synthetic resin molded articles in order to impart antimicrobial functions.

Methods which have been developed to impart antimicrobial properties to synthetic resins and the like include methods of adding compounds containing metals such as silver, gold and zinc to synthetic resins, and methods of adding zeolite-based solid particles ion-exchanged with silver ions or copper ions to synthetic resins.

However, such synthetic resin molded articles can also produce dermopathies in individuals depending on the purpose of use, and particularly in infants with weaker skin resistance or in allergic-prone individuals.

Other methods involve addition of highly safe naturally-derived antimicrobial compounds to synthetic resins. As such naturally-derived antimicrobial compounds there may be mentioned allyl isothiocyanates extracted from mustard or horseradish, protamines extracted from mature testicles of salmon, trout or the like, chitosan obtained by deacetylation of chitin extracted from crustaceans, and ε-polylysine obtained from microbes belonging to the genus *Streptomyces*.

However, although these naturally-derived antimicrobial compounds are highly safe, allyl isothiocyanates are volatile and therefore readily volatilize by heat during production of synthetic resin molded articles, and consequently they must be used in large amounts in order to impart an adequate antimicrobial function to antimicrobial synthetic resin molded articles, while protamines, being proteins, are poorly resistant to heat and therefore cannot withstand the working temperatures of synthetic resins. Also, chitosan is poorly soluble in solvents, and therefore without modification it is troublesome to use in synthetic resins.

ε-Polylysine is a polymer compound comprising lysine groups bonded together by acid amide bonds between the ε-amino groups and the hydroxycarbonyl groups of adjacent lysines. ε-Polylysine is highly stable, being a polymer of the essential amino acid lysine, and its high cation content gives it unique antimicrobial and other properties. Furthermore, because it is a polymer it has very low volatility and exhibits heat resistance. However, it is water-soluble and therefore has low solubility in solvents other than water and some alcoholic solvents.

Methods for modifying naturally-derived antimicrobial compounds include introduction of myristoyl groups into chitosan to enhance the emulsification properties (see Technical Document 1), and modification of protamines or ε-polylysine with dextran to enhance their emulsifying activity (see Technical Document 2). However, these methods are intended to impart or improve emulsification properties for naturally-derived antimicrobial compounds, and they do not improve the volatility, heat resistance or solubility in organic solvents, nor do they improve compatibility with resins. Needless to mention, because such compounds do not include silicone chains they do not exhibit the properties of silicone.

Polyorganosiloxanes can be blended with or copolymerized with various organic resins such as thermoplastic resins, thereby imparting the properties of polyorganosiloxanes such as weather resistance, surface water repellency, lubricity, low abrasiveness, biocompatibility, antithrombotic properties and gas permeability for efficacy as organic resin modifiers, and their uses in paints, adhesives, coating agents, fiber processing agents, inorganic material surface modifiers, toiletries, cosmetics and the like are known.

Naturally-derived antimicrobial compounds such as ε-polylysine are water-soluble and are therefore almost always used in aqueous systems and almost never employed in oil-based systems. On the other hand, polyorganosiloxanes are generally lipophilic and are therefore virtually insoluble in water. Certain types of polyorganosiloxanes which are water-soluble or have high affinity for water are known, however, such as non-ionic polyorganosiloxanes modified with polyethylene glycol or the like. Nevertheless, virtually no polycationic water-soluble polyorganosiloxanes or antimicrobial polyorganosiloxanes are known. Thus, while naturally-derived antimicrobial compounds such as ε-polylysine have been blended together with polyorganosiloxanes for their simultaneous use, it has been very difficult to achieve mixtures of the two. A third component such as a surfactant has therefore been necessary, thus requiring advanced emulsifying techniques. This has placed restrictions on the means currently employed for uniform mixing of naturally-derived antimicrobial agents, polyorganosiloxanes and resins.

The prior arts are disclosed in JP-A 54-147220/1979, JP-A 59-133235/1984, Japan Cosmetic Journal, Vol.26, No.2 (2002), Foods Food Ingredients J. Jpn. No.185(2002).

SUMMARY OF THE INVENTION

The present invention comprises the following items A, B, C and D.

A. ε-Polylysine represented by the following formula (1), having a polyorganosiloxane group introduced into the molecule (a polymer hereinafter referred to as "silicone-modified ε-polylysine").

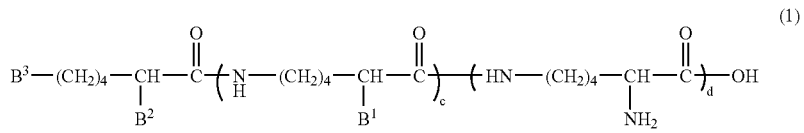

wherein $B^1$, $B^2$ and $B^3$ are groups represented by general formula (2) below or amino groups, and at least one thereof is a group represented by formula (2), c is an integer of 0 to 50, d is an integer of 0 to 50, and c+d is an integer of 1 to 50.

-D-Y-Q     (2)

wherein D is a group represented by:

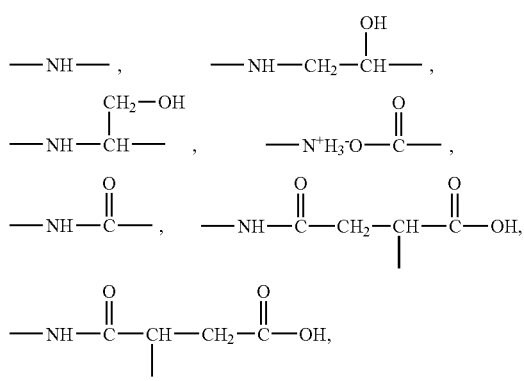

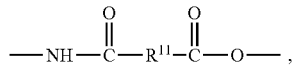

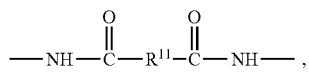

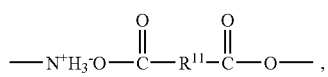

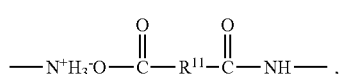

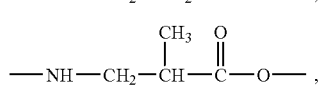

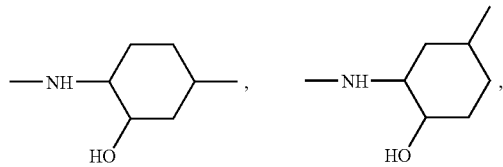

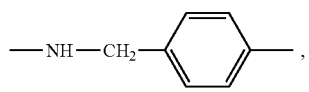

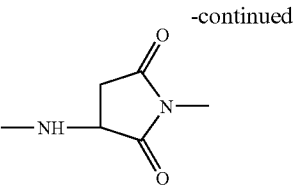

wherein $R^{11}$ is C1-5 linear or branched alkylene, C2-5 alkenylene or C6-10 arylene), and Y is C1-1000 linear or branched alkylene, of which any mutually non-adjacent methylenes may be substituted with —O—, and Q is a polyorganosiloxane group represented by the following formula (3):

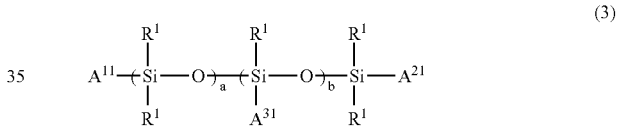

wherein each $R^1$ is independently C1-20 alkyl or C6-10 aryl, a is an integer of 0 to 1000, b is an integer of 0 to 1000, a+b is an integer of 1 to 1000, and $A^{11}$, $A^{21}$ and $A^{31}$ are independently $R^1$, a monovalent residue which is a compound represented by formula (1) with Q removed, or a single bond, with one thereof being a single bond.

B. A process for production of silicone-modified ε-polylysine represented by above formula (1), obtained by reacting ε-polylysine represented by the following formula (4) with a polyorganosiloxane having a functional group which can react with the amino groups of ε-polylysine.

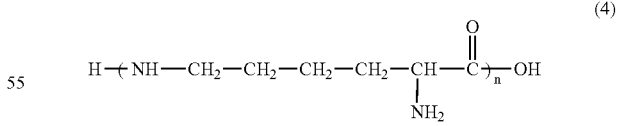

wherein n is a integer of 2 to 50.

C. An antimicrobial agent comprising an amino group-containing antimicrobial polymer having a polyorganosiloxane group introduced into the molecule (the polymer being hereinafter referred to as "silicone-modified antimicrobial polymer" and the antimicrobial agent being hereinafter referred to as "silicone-modified antimicrobial agent").

D. An antimicrobial resin composition comprising an antimicrobial agent according to item C and a resin.

DETAILED DESCRIPTIONS

Figure 1:
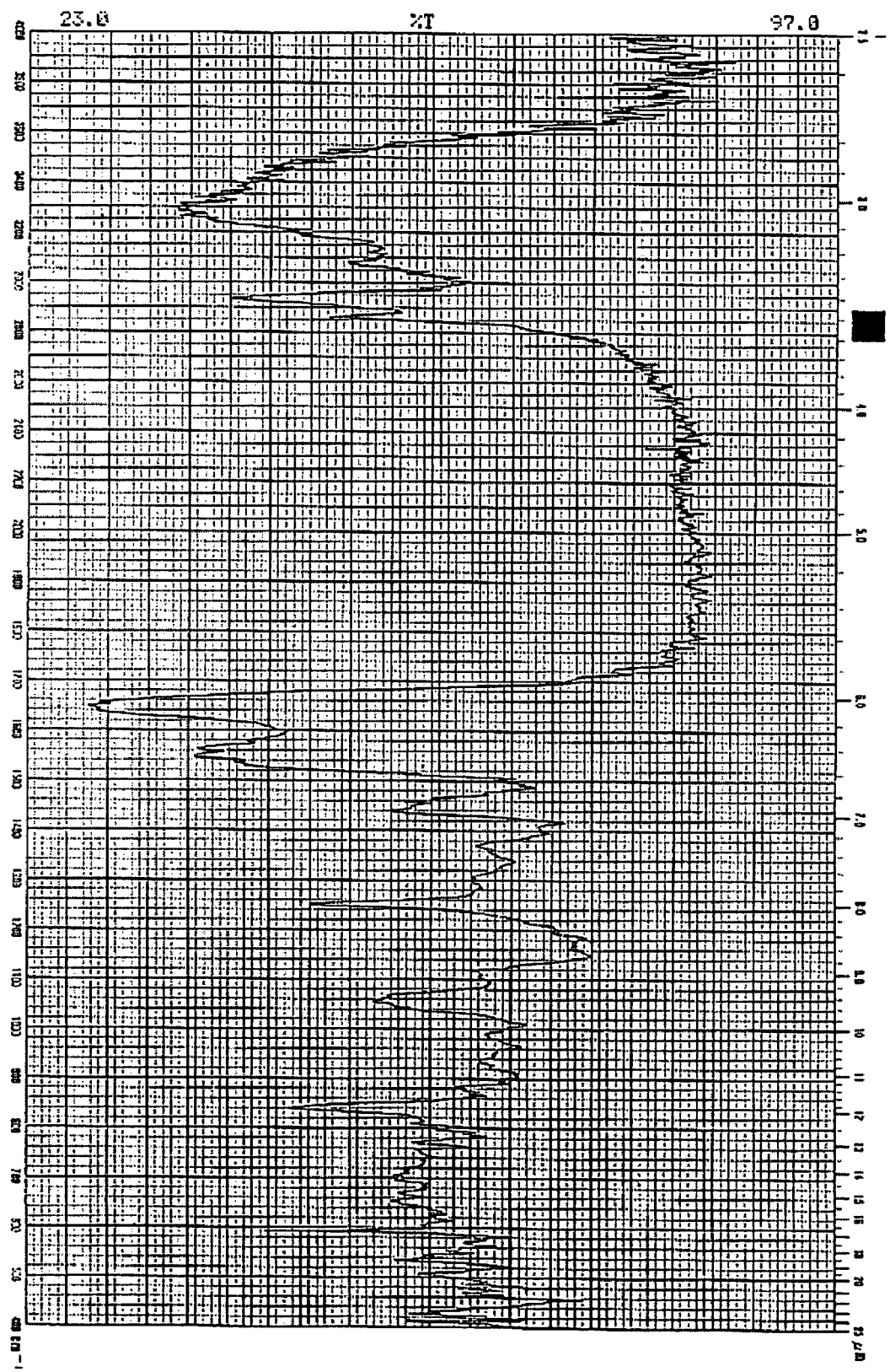
FIG. 1 shows an IR chart of the silicone-modified antimicrobial polymer obtained in Example 1 of the present invention.

The present inventors have carried out much avid research in light of the aforementioned problems of the prior art. As a result, we have completed the present invention upon finding that an amino group-containing antimicrobial polymer having a polyorganosiloxane group introduced into the molecule can be obtained by reacting a specific naturally-derived amino group-containing antimicrobial polymer with a polyorganosiloxane having a functional group which can react with amino groups, and upon further finding that such polymers exhibit antimicrobial activity, high solubility in organic solvents and thus excellent compatibility with resins, and are also highly safe.

The present invention has the following construction.

(1) Silicone-modified ε-polylysine represented by above formula (1).

(2) Silicone-modified ε-polylysine according to (1) above, wherein D in above formula (2) is one of the following groups.

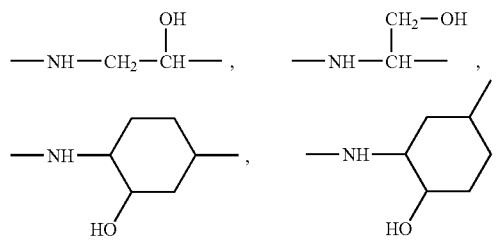

(3) Silicone-modified ε-polylysine according to (1) above, wherein D in formula (2) is one of the following groups.

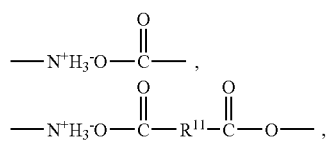

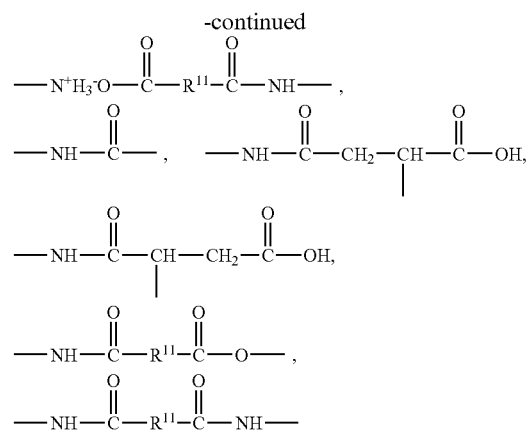

wherein $R^{11}$ is C1-5 linear or branched alkylene, C2-5 alkenylene or C6-10 arylene.

(4) Silicone-modified ε-polylysine according to (1) above, wherein D in formula (2) is one of the following groups.

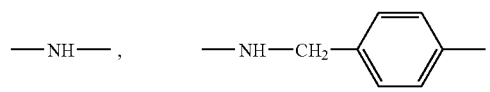

(5) Silicone-modified ε-polylysine according to (1) above, wherein D in formula (2) is one of the following groups.

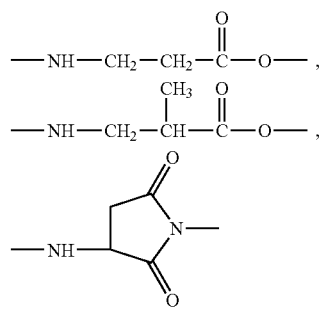

(6) A process for production of silicone-modified ε-polylysine represented by formula (1) above, obtained by reacting ε-polylysine represented by the formula (4) with a polyorganosiloxane having a functional group which can react with the amino groups of ε-polylysine.

(7) A process for production of silicone-modified ε-polylysine according to (6) above, wherein the polyorganosiloxane having a functional group which can react with the amino groups of ε-polylysine is a polyorganosiloxane with an epoxy group.

(8) A process for production of silicone-modified ε-polylysine according to (6) above, wherein the polyorganosiloxane having a functional group which can react with the amino groups of ε-polylysine is a polyorganosiloxane with carboxylic acid or a carboxylic acid derivative as the functional group.

(9) A process for production of silicone-modified ε-polylysine according to (6) above, wherein the polyorganosiloxane having a functional group which can react with the amino groups of ε-polylysine is a polyorganosiloxane with a halogenated alkyl group.

(10) A process for production of silicone-modified ε-polylysine according to (6) above, wherein the polyorganosiloxane having a functional group which can react with the amino groups of ε-polylysine is a polyorganosiloxane with an unsaturated group.

(11) A silicone-modified antimicrobial agent comprising a silicone-modified antimicrobial polymer.

(12) A silicone-modified antimicrobial agent according to (11) above, wherein the silicone-modified antimicrobial polymer is a polymer obtained by reacting an amino group-containing antimicrobial polymer and a polyorganosiloxane having a functional group which can react with amino groups, represented by formula (5) below.

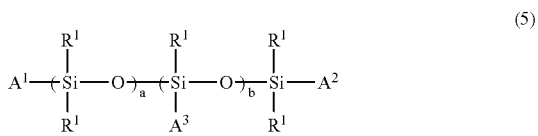

wherein $R^1$ is C1-20 alkyl or C6-10 aryl, a is an integer of 0 to 1000, b is an integer of 0 to 1000, a+b is an integer of 1 to 1000, $A^1$, $A^2$ and $A^3$ are each a group represented by formula (6) below, C1-20 alkyl or C6-10 aryl, and at least one among $A^1$, $A^2$ and $A^3$ is a group represented by formula (6),

-Y-Z  (6)

wherein Y represents C1-1000 alkylene, of which any mutually non-adjacent methylenes may be substituted with —O—, and Z is one of the following groups.

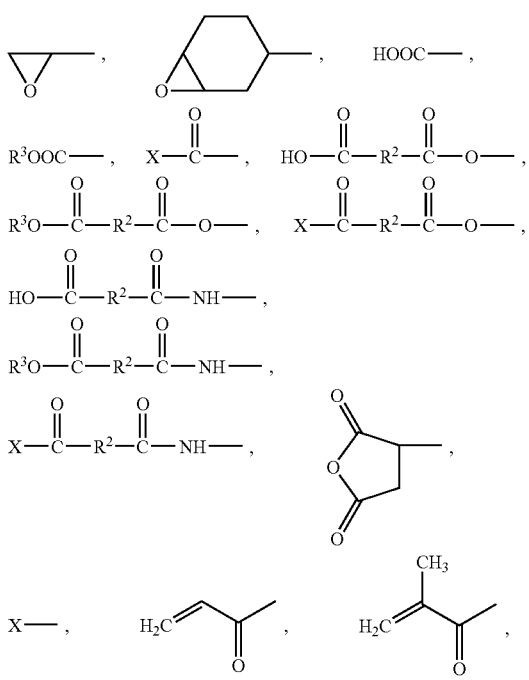

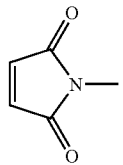

wherein $R^2$ is C1-5 alkylene, C2-5 alkenylene or C6-10 arylene, $R^3$ is C1-20 alkyl, C6-10 aryl or trimethylsilyl, and X is chlorine, bromine or iodine.

(13) A silicone-modified antimicrobial agent according to (12) above, wherein the amino group-containing antimicrobial polymer is ε-polylysine.

(14) A silicone-modified antimicrobial agent according to (12) or (13) above, wherein Z in formula (6) is one of the following groups.

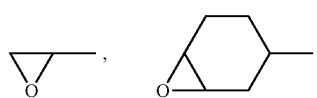

(15) A silicone-modified antimicrobial agent according to (12) or (13) above, wherein Z in formula (6) is one of the following groups.

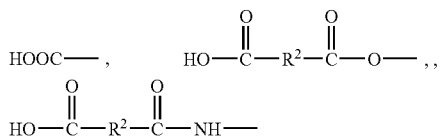

wherein $R^2$ is C1-5 alkylene, C2-5 alkenylene or C6-10 arylene.

(16) A silicone-modified antimicrobial agent according to (12) or (13) above, wherein Z in formula (6) is one of the following groups.

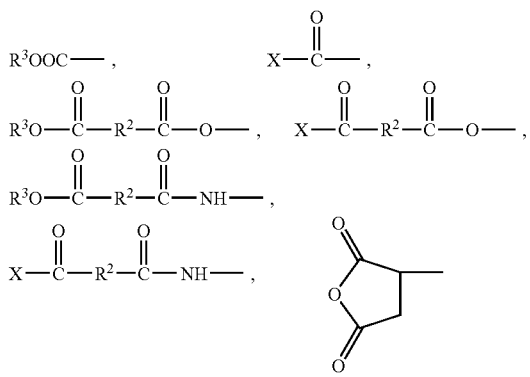

wherein $R^2$ is C1-5 alkylene, C2-5 alkenylene or C6-10 arylene, $R^3$ is C1-20 alkyl, C6-10 aryl or trimethylsilyl, and X is chlorine, bromine or iodine.

(17) A silicone-modified antimicrobial agent according to (12) or (13) above, wherein Z in formula (6) is chlorine, bromine or iodine.

(18) A silicone-modified antimicrobial agent according to (12) or (13) above, wherein Z in formula (6) is one of the following groups.

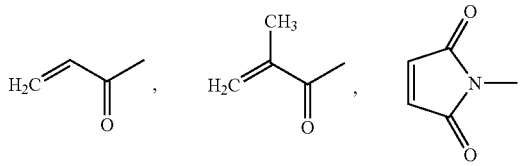

(19) An antimicrobial agent according to (12) above, wherein the residual ratio of the number of amino groups of the amino group-containing antimicrobial polymer is 10-99%.

(20) An antimicrobial resin composition comprising an antimicrobial agent according to any one of (11) to (19) above and a resin.

(21) An antimicrobial resin composition according to (20) above, wherein the resin is a synthetic resin.

(22) An antimicrobial resin composition according to (21) above, wherein the synthetic resin is a vinyl-based polymer.

(23) An antimicrobial resin composition according to (21) above, wherein the synthetic resin is a polyolefin-based resin.

(24) An antimicrobial resin composition according to (21) above, wherein the synthetic resin is a silicone-based resin.

(25) An antimicrobial resin composition according to (21) above, wherein the synthetic resin is an acrylic resin.

(26) An antimicrobial resin composition according to (21) above, wherein the synthetic resin is an epoxy resin.

The amino group-containing antimicrobial polymer according to the invention is a compound containing amino groups in the polymer molecule and exhibiting antimicrobial activity, and it may be a naturally-derived compound or a synthetically-produced compound. Specifically, there may be mentioned α-polylysine, ε-polylysine, chitosan, protamines, lactoferrin and the like. Preferred among these are the naturally-derived compounds ε-polylysine, chitosan and protamines, and most preferred is ε-polylysine which is thermally stable and relatively easily soluble in solvents.

ε-Polylysine may be obtained, specifically, by culturing *Streptomyces albulus* subsp. *lysinopolymerus* disclosed in Japanese Patent No. 1245361 in medium having a composition of 5 wt % glucose, 0.5 wt % yeast extract, 1 wt % ammonium sulfate, 0.08 wt % dipotassium hydrogen phosphate, 0.136 wt % potassium dihydrogen phosphate, 0.05 wt % magnesium sulfate heptahydrate, 0.004 wt % zinc sulfate heptahydrate and 0.03 wt % iron sulfate heptahydrate, and adjusted to a pH of 6.8, and separating and recovering ε-polylysine from the obtained culture product. There may also be mentioned ε-polylysine obtained by decomposing this with an acid, alkali or enzyme to an appropriate molecular weight.

As polyorganosiloxanes having functional groups which can react with amino groups there may be mentioned polyorganosiloxanes having epoxy groups, polyorganosiloxanes having carboxylic acid or carboxylic acid derivatives as functional groups, polyorganosiloxanes having halogenated alkyl groups and polyorganosiloxanes having unsaturated groups. According to the invention, the polyorganosiloxane having a functional group which can react with amino groups is preferably a polyorganosiloxane having an epoxy group.

In general formula (5) above, $R^1$ is C1-20 alkyl, among which there may be mentioned methyl, ethyl, n-propyl, i-propyl, n-butyl, i-butyl, s-butyl, t-butyl, pentyl, neopentyl, hexyl, heptyl, octyl, nonyl, decyl, undecyl, dodecyl, cyclopentyl, cyclohexyl, benzyl and phenethyl, or C6-10 aryl among which there may be mentioned phenyl, toluyl, xylyl and ethylphenyl.

Also in general formula (5) above, a is an integer of 0 to 1000, b is an integer of 0-1000 and a+b is an integer of 1 to 1000. $A^1$, $A^2$ and $A^3$ are each a group represented by formula (6) above, C1-20 alkyl, among which there may be mentioned methyl, ethyl, n-propyl, i-propyl, n-butyl, i-butyl, s-butyl, t-butyl, pentyl, neopentyl, hexyl, heptyl, octyl, nonyl, decyl, undecyl, dodecyl, cyclopentyl, cyclohexyl, benzyl and phenethyl, or C6-10 aryl, among which there may be mentioned phenyl, toluyl, xylyl and ethylphenyl. At least one from among $A^1$, $A^2$ and $A^3$ must be a group represented by general formula (2).

In general formula (2) or (6) above, Y represents C1-1000 alkyl, of which any mutually non-adjacent methylenes may be substituted with —O—. As specific examples there may be mentioned ethylene, trimethylene, tetramethylene, pentamethylene, hexamethylene, heptamethylene, octamethylene, nonamethylene, decamethylene, undecamethylene, dodecamethylene, tetradecamethylene, 2-methylethylene, 2-methyltrimethylene, 2-methyltetramethylene, 2-methylpentamethylene, 2-methylhexamethylene, 2-methylheptamethylene, 2-methyloctamethylene, 2-methylnonamethylene, 2-methyldecamethylene, 2-methylundecamethylene, —CH$_2$CH$_2$CH$_2$O—, —CH$_2$CH$_2$CH$_2$OCH$_2$CH$_2$O—, —CH$_2$CH$_2$CH$_2$OCH$_2$—, or —CH$_2$CH$_2$CH$_2$O(CH$_2$CH$_2$O)$_m$—, —CH$_2$CH$_2$CH$_2$O(CH$_2$CH(CH$_3$)O)$_m$— or —CH$_2$CH$_2$CH$_2$O(CH(CH$_3$)CH$_2$O)$_m$— where m is an integer of 1 or greater.

According to the invention, Y is not particularly restricted but among the groups mentioned above, it is preferably trimethylene, decamethylene, 2-methylethylene, —CH$_2$CH$_2$CH$_2$O—, —CH$_2$CH$_2$CH$_2$OCH$_2$CH$_2$O—, —CH$_2$CH$_2$CH$_2$OCH$_2$— or —CH$_2$CH$_2$CH$_2$O(CH$_2$CH$_2$O)$_m$— where m is an integer of 1 or greater.

In general formula (6) above, Z is any of the groups mentioned above.

More specifically, as C1-5 alkylene groups for $R^2$ there may be mentioned linear or branched alkylene groups such as —CH$_2$CH$_2$—, —CH$_2$—CH(—CH$_3$)—, —CH$_2$CH(—C$_2$H$_5$)— and —CH(—CH$_3$)—CH(—CH$_3$)—, and as C2-5 alkenylene groups there may be mentioned linear or branched alkenylene groups such as —CH═CH—, —CH$_2$—C(═CH$_2$)—, —CH═C(—CH$_3$)— and —C(CH$_3$)═C(—CH$_3$)—.

As C6-10 arylene groups there may be mentioned 1,2-phenylene, 4-methyl-1,2-phenylene, dimethyl-1,2-phenylene and 4-ethyl-1,2-phenylene. According to the invention, $R^2$ is not particularly restricted but is preferably —CH$_2$CH$_2$—, —CH═CH—, —CH$_2$—C(═CH$_2$)—, —CH═C(—CH$_3$)— or 1,2-phenylene.

$R^3$ is C1-20 alkyl, C6-10 aryl or trimethylsilyl, and as C1-20 alkyl groups there may be mentioned methyl, ethyl, n-propyl, i-propyl, n-butyl, i-butyl, s-butyl, t-butyl, pentyl, neopentyl, hexyl, heptyl, octyl, nonyl, decyl, undecyl, dodecyl, cyclopentyl, cyclohexyl, benzyl and phenethyl, while as C6-10 aryl groups there may be mentioned phenyl, toluyl, xylyl and ethylphenyl.

As polyorganosiloxanes having functional groups which can react with amino groups there may be mentioned single end-modified polyorganosiloxanes having a functional group at one end, dual end-modified polyorganosiloxanes having functional groups at both ends, and side chain-modified polyorganosiloxanes having functional groups on side chains.

Although any such polyorganosiloxanes may be used according to the invention, dual end-modified polyorganosiloxanes and side chain-modified polyorganosiloxanes having multiple functional groups, which have more than one functional group in each molecule, can result in gelling of the silicone-modified antimicrobial polymer obtained by the reaction. Therefore, single end-modified polyorganosiloxanes or side chain-modified polyorganosiloxanes having one functional group are preferably used.

The silicone-modified antimicrobial polymer obtained by reaction between the amino group-containing antimicrobial polymer and the polyorganosiloxane having a functional group which can react with amino groups according to the invention is obtained by reacting an amino group-containing antimicrobial polymer with a polyorganosiloxane having a functional group which can react with amino groups represented by general formula (5) above, in a solvent. For the reaction, the polyorganosiloxane having a functional group which can react with amino groups may be reacted in an equimolar amount with the amino groups in the amino group-containing antimicrobial polymer. However, a certain number of amino groups must remain in order to impart an antimicrobial property as a silicone-modified antimicrobial agent. The residual ratio of the number of amino groups after the reaction is preferably 10-99% and more preferably 50-99%.

The polyorganosiloxane content in the silicone-modified antimicrobial polymer obtained by reaction between the amino group-containing antimicrobial polymer and the polyorganosiloxane having a functional group which can react with amino groups may be controlled by the charging ratio of the polyorganosiloxane having a functional group which can react with amino groups with respect to the amino group-containing antimicrobial polymer, and by the molecular weight of the polyorganosiloxane. The polyorganosiloxane content is 1-99 wt % and preferably 10-90 wt %. A polyorganosiloxane content of less than 1 wt % reduces the effect of introducing the polyorganosiloxane, i.e. the effect of enhancing the solubility in solvents and the water repellency, while a content of greater than 99 wt % reduces the antimicrobial property.

The solvent used for the reaction is not particularly restricted so long as it is a solvent in which the amino group-containing antimicrobial polymer dissolves, and for example, there may be mentioned methanol, ethanol, 2-propanol, water-methanol mixed solvents, water-ethanol mixed solvents, water-dimethylformamide mixed solvents, methanol-2-propanol mixed solvents, methanol-ethanol mixed solvents and ethanol-2-propanol mixed solvents. The amount of reaction solvent used is 1-100 times and preferably 1-10 times the weight of the amino group-containing antimicrobial polymer. The reaction temperature does not necessarily need to be a high temperature as the reaction is expected to proceed even at room temperature, but since the reaction time will be lengthened at lower temperatures, it is preferably 30-70° C.

The reaction is conducted by dissolving the amino group-containing antimicrobial polymer in the solvent and then adding dropwise the polyorganosiloxane having a functional group which can react with amino groups. The dropwise addition time is preferably 0.01-2 hours. The reaction between the functional groups and amino groups is expected to proceed within a short time, but the reaction time is preferably 1-24 hours. Since it is possible that the polyorganosiloxane having a functional group which can react with amino groups may not readily dissolve in the solvent, stirring is preferably carried out at a speed which ensures adequate mixing. After completion of the reaction, the solvent may be distilled off to obtain the silicone-modified antimicrobial polymer.

There are no particular restrictions on the amount of a silicone-modified antimicrobial agent of the invention used, but considering the increased costs incurred with large volume use, it is preferably 0.0001-50 wt % and more preferably 0.001-20 wt %.

As resins to be used in the antimicrobial resin composition of the invention there may be mentioned vinyl-based polymers such as acrylic resins, vinyl chloride resins, vinylidene chloride resins and vinyl acetate resins; polyolefin-based resins such as polypropylene, binary or tertially crystalline copolymers with other $\alpha$-olefin, low-density polyethylene, linear low-density polyethylene, high density polyethylene resins, ethylene-propylene copolymer rubber; polystyrene-based reseins such as polystyrene, acrylonitrile-butadiene-styrene copolymer, styrene-butadiene copolymer thermoplastic elastomers; silicon-based resins such as polyorganosiloxanes; and other synthetic resins such as phenol resins, alkyd resins, melamine-alkyd resins, polyester resins, polyamide resins, polyamideimide resins, polyimide resins, epoxy resins, polyurethane resins and polyurea resins, as well as lacquers, boiled oils, oil-based varnishes and oil-based enamels. Preferred among these are vinyl-based polymers such as acrylic resins, polyolefin-based resins, silicon-based resins and epoxy resins.

The antimicrobial resin composition of the invention may be obtained by blending the resin with the silicone-modified antimicrobial agent. The blending method is not particularly restricted, and is sufficient if it produces a uniform blend of the resin and the silicone-modified antimicrobial agent. An example of an effective method is blending by dissolving the resin and the silicone-modified antimicrobial agent in a common solvent. Alternatively, they may be blended during melt molding.

As specific examples of common solvents for the resin and the silicone-modified antimicrobial agent there may be mentioned hydrocarbons such as toluene, xylene, n-hexane and cyclohexane, alcohols such as methanol, ethanol and 2-propanol, ethers such as diethyl ether and tetrahydrofuran, and amides such as N,N-dimethylformamide and N,N-dimethylacetamide, of which one or a combination of two or more may be used. The silicone-modified antimicrobial agent and the resin will often dissolve in such solvents at room temperature, but in cases where they do not dissolve, dissolution may be induced by heating to a degree which does not alter the silicone-modified antimicrobial agent and resin.

There are no particular restrictions on the amount of silicone-modified antimicrobial agent added, but the content of the silicone-modified antimicrobial agent in the antimicrobial resin composition is preferably 0.0001-50 wt % and more preferably 0.001-20 wt %.

The antimicrobial resin composition of the invention may be provided as an intermediate product, in the form of pellets for molding or a solvent-dissolved resin composition for coating. Such intermediate products are worked into the final products such as molded articles, fibers, films or sheets, for practical use.

When the use is as a molded article, the production process employed may be any of various production processes selected according to the resin used in the antimicrobial resin composition, and generally speaking there may be mentioned extrusion molding, calender molding and injection molding as common processes for molding of thermoplastic resins, or compression molding and transfer molding as common processes for molding of thermosetting resins.

In this case, various additives commonly employed in ordinary synthetic resins may be added.

Such additives include heat stabilizers to impart heat stability, heat degradation resistance and heat resistance, weather resistance agents to impart weather resistance, light fastness agents to impart light fastness, various stabilizers to impart functionality, neutralizers, adjuncts, surfactants, organic or inorganic pigments, organic or inorganic fillers for enhanced mechanical strength and functionality of molded articles, etc. If necessary, antimicrobial aids may also be used to increase the antimicrobial property of the silicone-modified antimicrobial agent.

When used as a resin composition for coating, the antimicrobial resin composition of the invention is dissolved in a solvent which can uniformly dissolve it.

Any solvent may be used for the dissolution so long as it uniformly dissolves the antimicrobial resin composition. As specific examples there may be mentioned hydrocarbons such as toluene, xylene, n-hexane and cyclohexane, alcohols such as methanol, ethanol and 2-propanol, acetic acid esters such as ethyl acetate and butyl acetate, ethers such as cellosolve acetate and propyleneglycol methyl ether acetate, ketones such as acetone, methyl ethyl ketone, ethyl acetoacetate, acetylacetone, methyl isobutyl ketone and diacetone alcohol and amides such as N,N-dimethylformamide and N,N-dimethylacetamide, of which any one or combination of two or more may be used.

The concentration of a resin composition for coating is not particularly restricted so long as the solution is homogeneous, but from the standpoint of facilitating coating it is preferably. 1-80 wt % and more preferably 10-50 wt %.

When the use is as a resin composition for coating, various additives may also be added as necessary. As suitable additives there may be mentioned curing agents, pigments, dispersing agents, antifoaming agents, thickeners, anti-settling agents, anti-sagging agents, leveling agents, delustering agents, anti-friction agents, ultraviolet absorbers, photostabilizers, antioxidants, antimicrobial aids and the like.

Coating of a resin composition for coating may be accomplished by a roll coater method, spin coater method, blade coater method, gravure coater method, beat coater method, curtain flow coater method or spray painting method, and either side or both sides of the substrate may be coated. The coating is preferably followed by heat drying at a temperature of 100° C. or above for 1 to 240 minutes and preferably 5 to 120 minutes during the film formation from the standpoint of performance of the obtained coating. A temperature of below 100° C. may result in inadequate removal of the solvent.

As coating substrates for the antimicrobial resin composition there may be mentioned metals, inorganic materials, plastics and composite materials. As metals there may be mentioned stainless steel, aluminum, tin sheets, galvanized sheets, soft steel sheets, copper, brass, various plated steel sheets, titanium, and the like. Substrates which have been surface-treated by chemical conversion treatment or alumite treatment may also be suitably used. As inorganic materials there may be mentioned glass, mortar, slate, concrete, clay tiles and the like. As plastics there may be mentioned polypropylene, polyethylene, acryl, polycarbonate, polystyrene, PET, nylon, polyester, rubber and elastomer plastic molded articles and film products. As composite materials there may be mentioned FRP, FRTP, laminated boards and sandwich materials obtained by contact bonding of metals and organic substances.

EXAMPLES

Examples will now described for further explanation, with the understanding that the invention is not limited to these examples.

1. Synthesis of Silicone-modified Antimicrobial Polymers

Example 1

After placing 10.0 g of ε-polylysine (number-average molecular weight=4090, measured by GPC-LALLS, same hereunder) and 30 g of methanol in a 100 milliliter three-necked flask equipped with a magnetic stirrer, condenser tube and thermometer, the mixture was stirred at room temperature for dissolution of the ε-polylysine. The temperature was raised to 50° C., and then 2.1 g ($8.05 \times 10^{-3}$ mol) of (3-glycidoxypropyl)-pentamethyldisiloxane represented by the following formula (7):

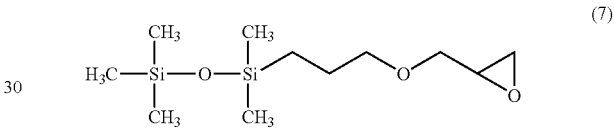

was added dropwise over a period of 5 minutes. Reaction was conducted for 3 hours while maintaining a temperature of 50° C. After the period of 3 hours, the reaction mixture was cooled and 10.0 g of ethanol was added. The volatile portion of the reaction mixture was then distilled off under reduced pressure using an evaporator to obtain 11.8 g of the product, silicone-modified antimicrobial polymer (1) comprising silicone-modified ε-polylysine, as a faint yellow solid. The structure of the product was confirmed by infrared absorption spectrum analysis (FIG. 1). The residual ratio of the number of amino groups of the polymer was 91%, and the silicone/ε-polylysine ratio was 17/83 (by weight).

Example 2

Figure 2:
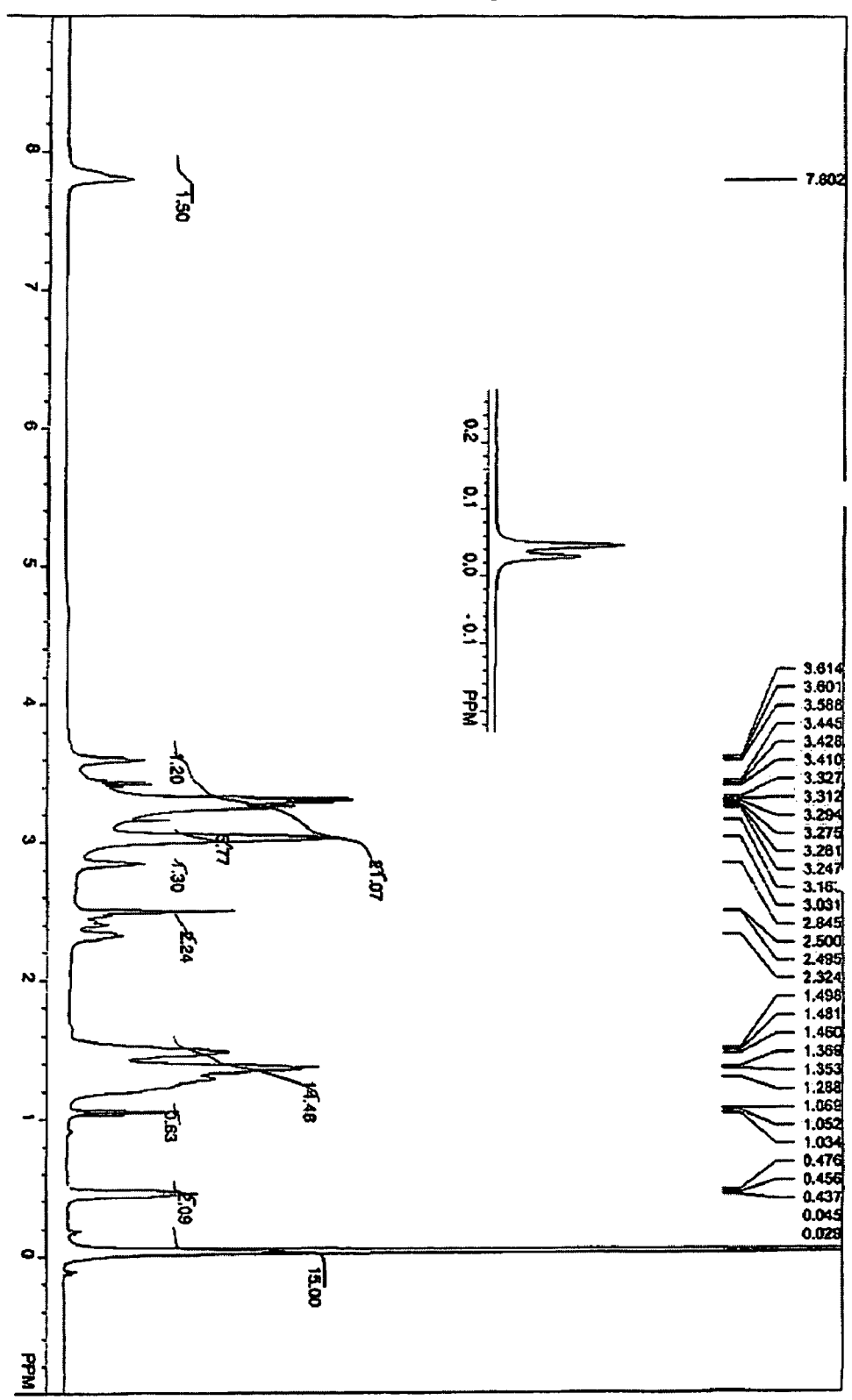
FIG. 2 shows a $^1$H-NMR chart of the silicone-modified antimicrobial polymer obtained in Example 2 of the present invention.

After placing 5.0 g of ε-polylysine (number-average molecular weight=4090) and 30.0 g of methanol in a 100 milliliter three-necked flask equipped with a magnetic stirrer, condenser tube and thermometer, the mixture was stirred at room temperature for dissolution of the ε-polylysine. The temperature was raised to 50° C., and then 5.0 g ($33.8 \times 10^{-3}$ mol) of (3-glycidoxypropyl)-pentamethyldisiloxane was added dropwise over a period of 10 minutes. Reaction was conducted for 3 hours while maintaining a temperature of 50° C. After the period of 3 hours, the reaction mixture was cooled and 10.0 g of ethanol was added. The volatile portion of the reaction mixture was then distilled off under reduced pressure using an evaporator to obtain 10.0 g of the product, silicone-modified antimicrobial polymer (2) comprising silicone-modified ε-polylysine, as a yellow jelly-like compound. The structure of the product was confirmed by nuclear magnetic resonance spectrum analysis (FIG. 2). The residual ratio of the number of amino groups of the polymer was 50%, and the silicone/ε-polylysine ratio was 50/50 (by weight).

Example 3

After placing 10.0 g of ε-polylysine (number-average molecular weight=4090) and 20.0 g of methanol in a 100 milliliter three-necked flask equipped with a magnetic stirrer, condenser tube and thermometer, the mixture was stirred at room temperature for dissolution of the ε-polylysine. Next, 20.0 g of 2-propanol was added, the temperature was raised to 70° C., and then 2.9 g of polydimethylsiloxane with a number-average molecular weight of 1000 represented by the following formula (8):

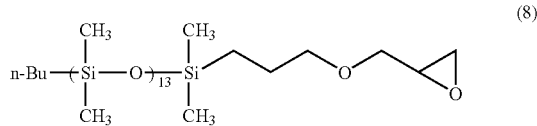

Figure 3:
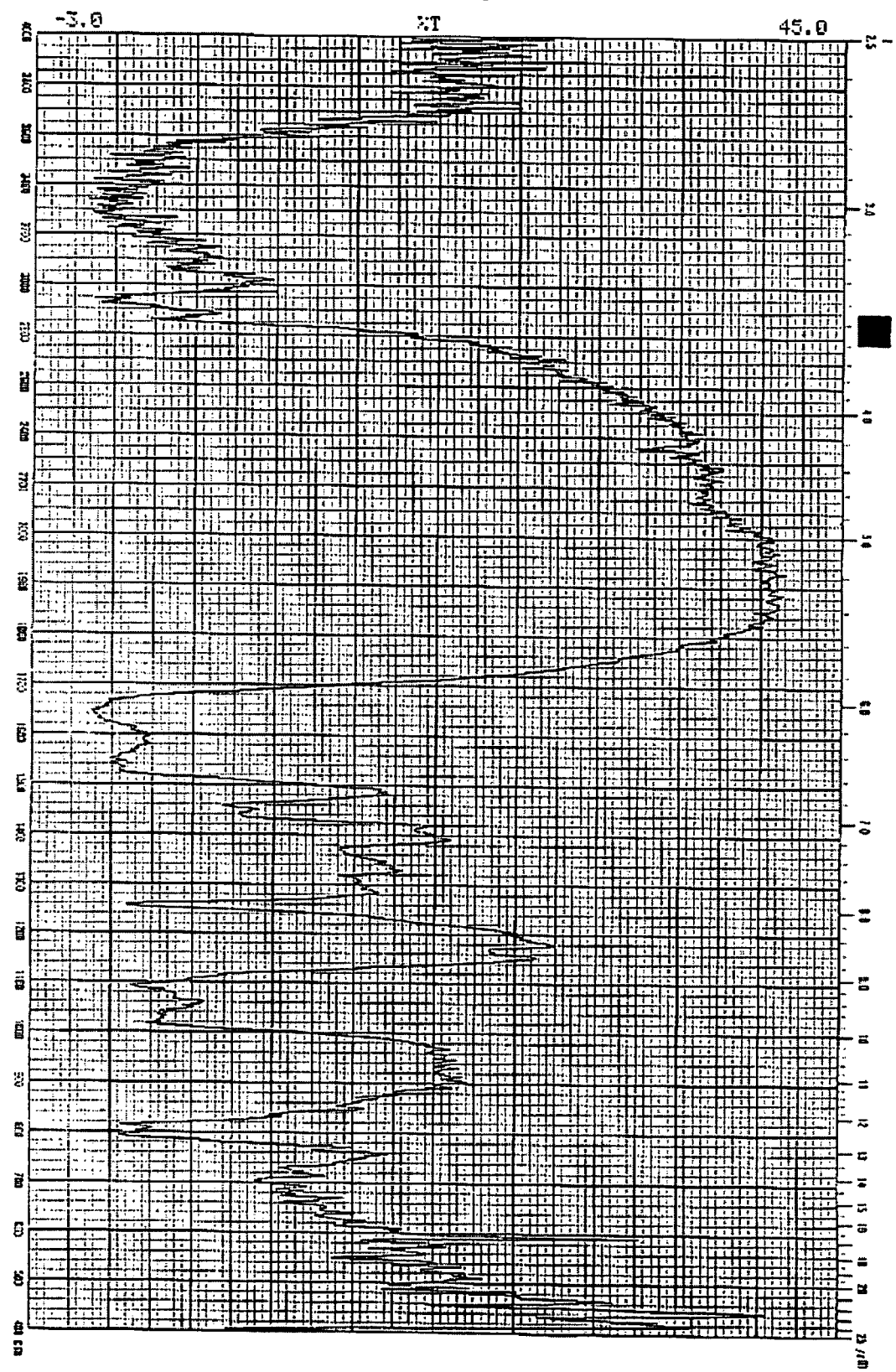
FIG. 3 shows an IR chart of the silicone-modified antimicrobial polymer obtained in Example 3 of the present invention.

(8)

having an epoxy group at one end was added dropwise over a period of 5 minutes. Reaction was conducted for 3 hours while maintaining a temperature of 70° C. The reaction mixture was cooled to room temperature, and then the volatile portion of the reaction mixture was distilled off under reduced pressure using an evaporator to obtain 12.6 g of the product, silicone-modified antimicrobial polymer (3) comprising silicone-modified ε-polylysine, as a faint yellow solid. The structure of the product was confirmed by infrared absorption spectrum analysis (FIG. 3). The residual ratio of the number of amino groups of the polymer was 97%, and the silicone/ε-polylysine ratio was 23/77 (by weight).

Example 4

Figure 4:
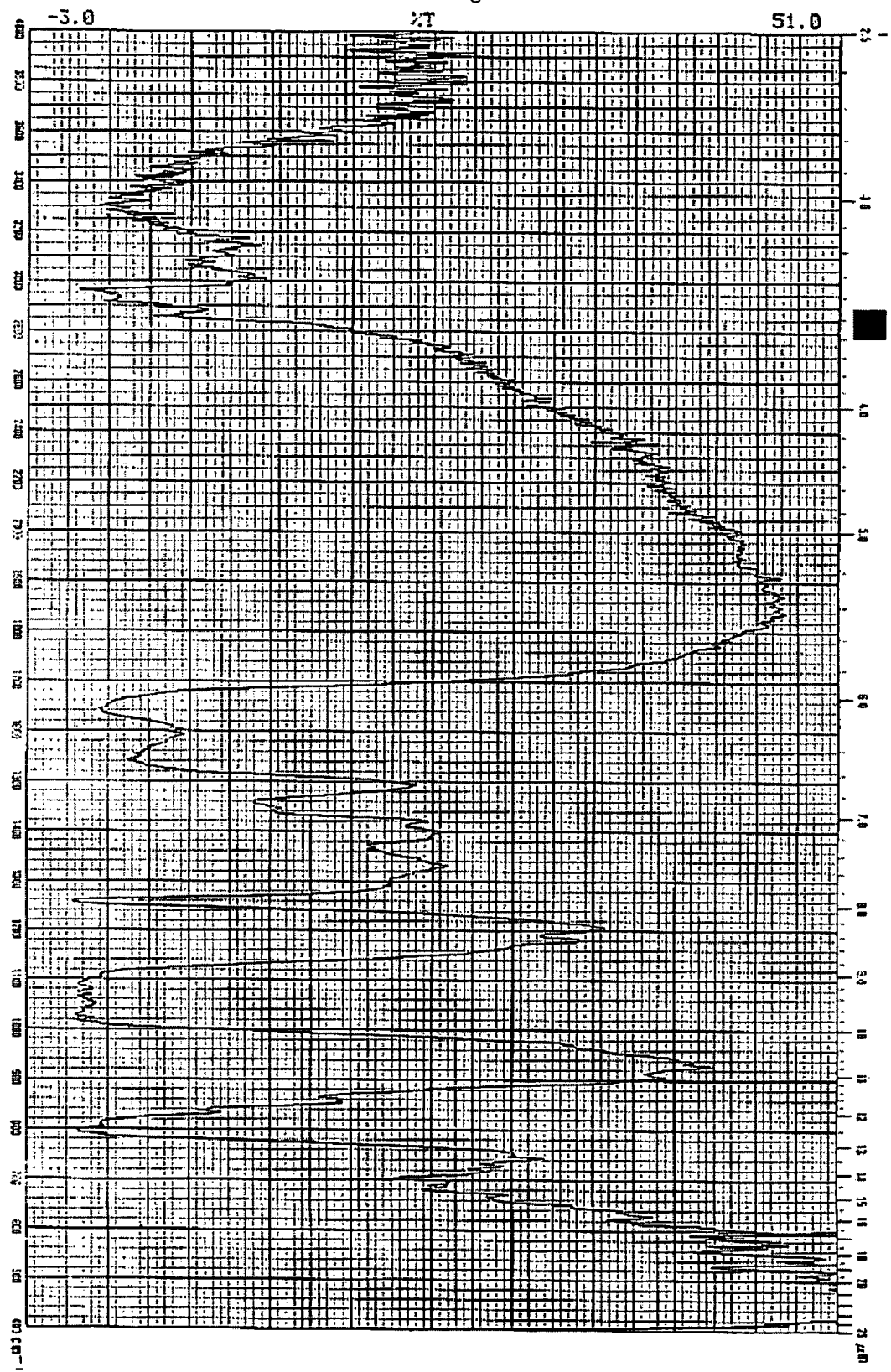
FIG. 4 shows an IR chart of the silicone-modified antimicrobial polymer obtained in Example 4 of the present invention.

After placing 5.0 g of ε-polylysine (number-average molecular weight=4090) and 20.0 g of methanol in a 100 milliliter three-necked flask equipped with a magnetic stirrer, condenser tube and thermometer, the mixture was stirred at room temperature for dissolution of the ε-polylysine. Next, 20.0 g of 2-propanol was added, the temperature was raised to 70° C., and then 5.0 g of the same polydimethylsiloxane used in Example 3, with a number-average molecular weight of 1000 and having an epoxy group at one end, was added dropwise over a period of 5 minutes. Reaction was conducted for 3 hours while maintaining a temperature of 70° C. The reaction mixture was cooled to room temperature, and then the volatile portion of the reaction mixture was distilled off under reduced pressure using an evaporator to obtain 9.9 g of the product, silicone-modified antimicrobial polymer (4) comprising silicone-modified ε-polylysine, as a faint yellow solid. The structure of the product was confirmed by infrared absorption spectrum analysis (FIG. 4). The residual ratio of the number of amino groups of the polymer was 91%, the silicone/ε-polylysine ratio was 50/50 (by weight), and the Si content was 15.8%.

Example 5

After placing 3.0 g of ε-polylysine (number-average molecular weight=4090) and 20.0 g of methanol in a 100 milliliter three-necked flask equipped with a magnetic stirrer, condenser tube and thermometer, the mixture was stirred at room temperature for dissolution of the ε-polylysine. Next, 20.0 g of 2-propanol was added, the temperature was raised to 70° C., and then 10.0 g of the same polydimethylsiloxane used in Example 3, with a number-average molecular weight of 1000 and having an epoxy group at one end, was added dropwise over a period of 10 minutes. Reaction was conducted for 3 hours while maintaining a temperature of 70° C. The reaction mixture was cooled to room temperature, and then the volatile portion of the reaction mixture was distilled off under reduced pressure using an evaporator to obtain 12.6 g of the product, silicone-modified antimicrobial polymer (5) comprising silicone-modified ε-polylysine, as a yellowish-white viscous liquid. The residual ratio of the number of amino groups of the polymer was 63%, and the silicone/ε-polylysine ratio was 77/23 (by weight).

Example 6

After placing 5.00 g of ε-polylysine (number-average molecular weight=4090) and 20.0 g of methanol in a 100 milliliter three-necked flask equipped with a magnetic stirrer, condenser tube and thermometer, the mixture was stirred at room temperature for dissolution of the ε-polylysine. Next, 20.0 g of 2-propanol was added, the temperature was raised to 70° C., and then 6.12 g of polydimethylsiloxane with a number-average molecular weight of 5000 represented by the following formula (9):

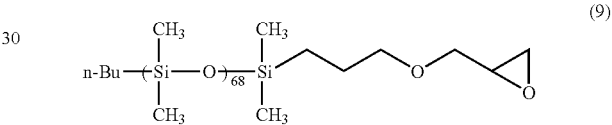

Figure 5:
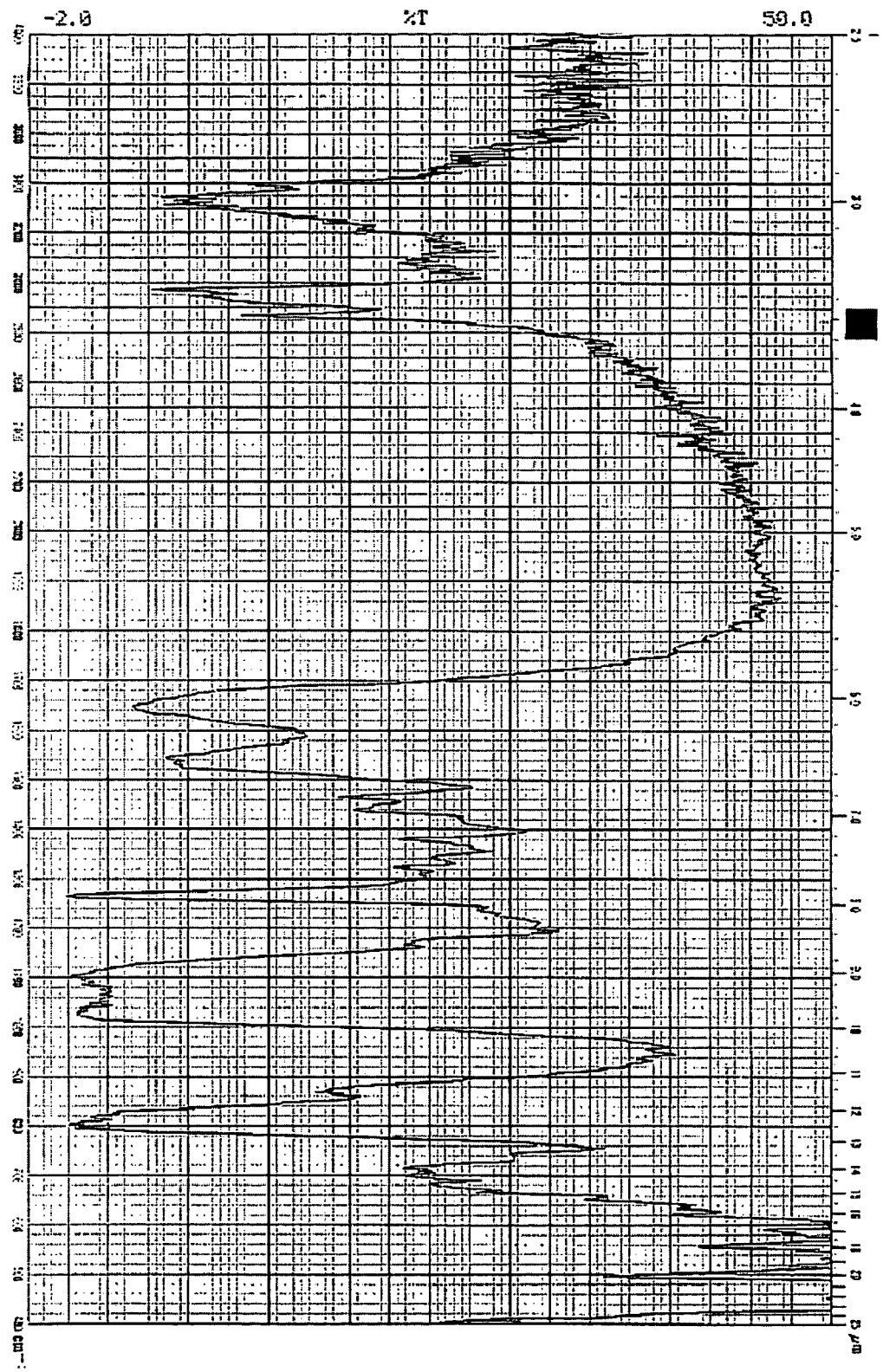
FIG. 5 shows an IR chart of the silicone-modified antimicrobial polymer obtained in Example 6 of the present invention.

(9)

having an epoxy group at one end was added dropwise over a period of 5 minutes. Reaction was conducted for 3 hours while maintaining a temperature of 70° C. The reaction mixture was cooled to room temperature, and then the volatile portion of the reaction mixture was distilled off under reduced pressure using an evaporator to obtain 11.1 g of the product, silicone-modified antimicrobial polymer (6) comprising silicone-modified ε-polylysine, as a faint yellow solid. The structure of the product was confirmed by infrared absorption spectrum analysis (FIG. 5). The residual ratio of the number of amino groups of the polymer was 97%, and the silicone/ε-polylysine ratio was 55/45 (by weight).

Example 7

Figure 6:
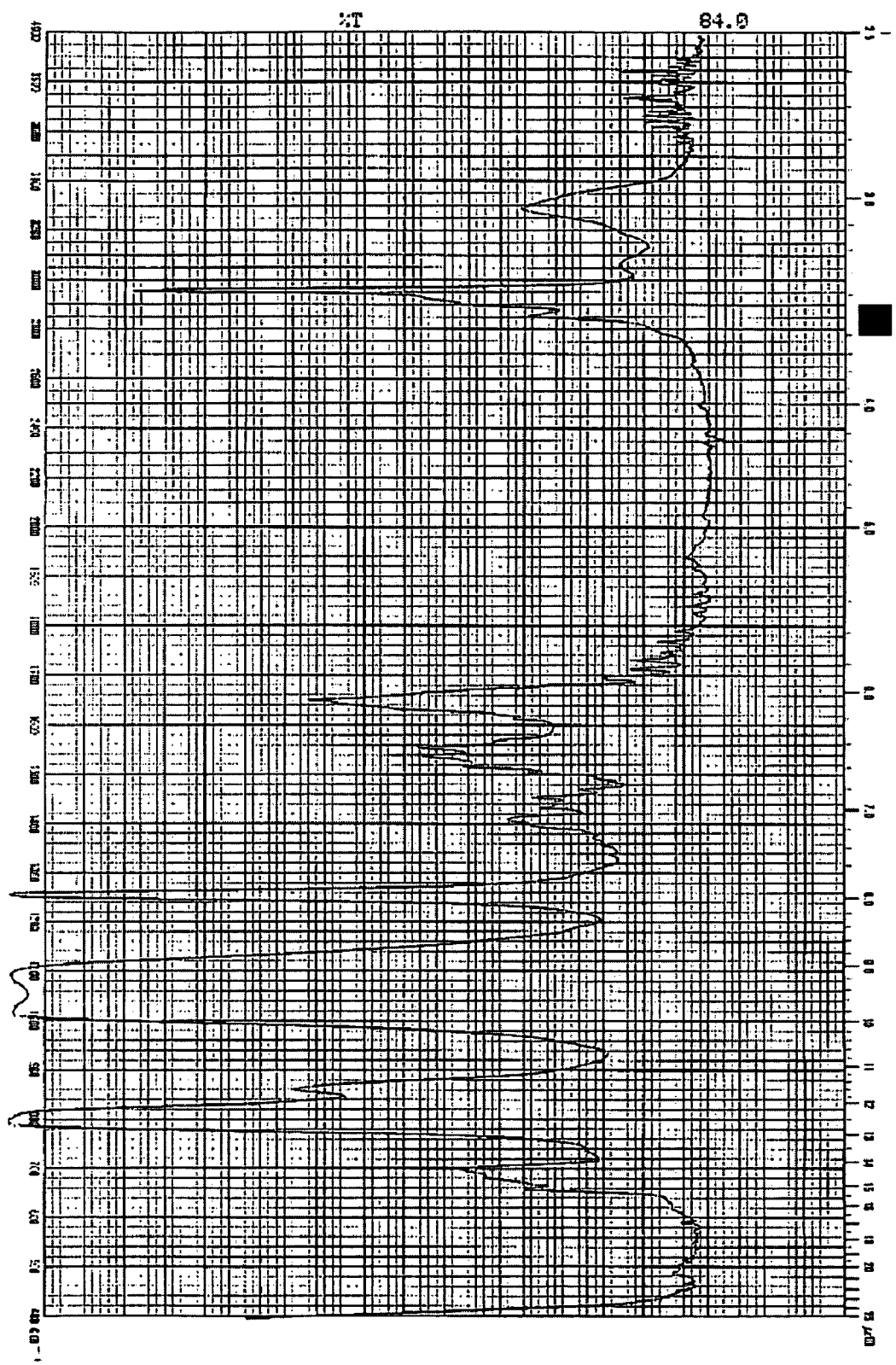
FIG. 6 shows an IR chart of the silicone-modified antimicrobial polymer obtained in Example 7 of the present invention.
Figure 7:
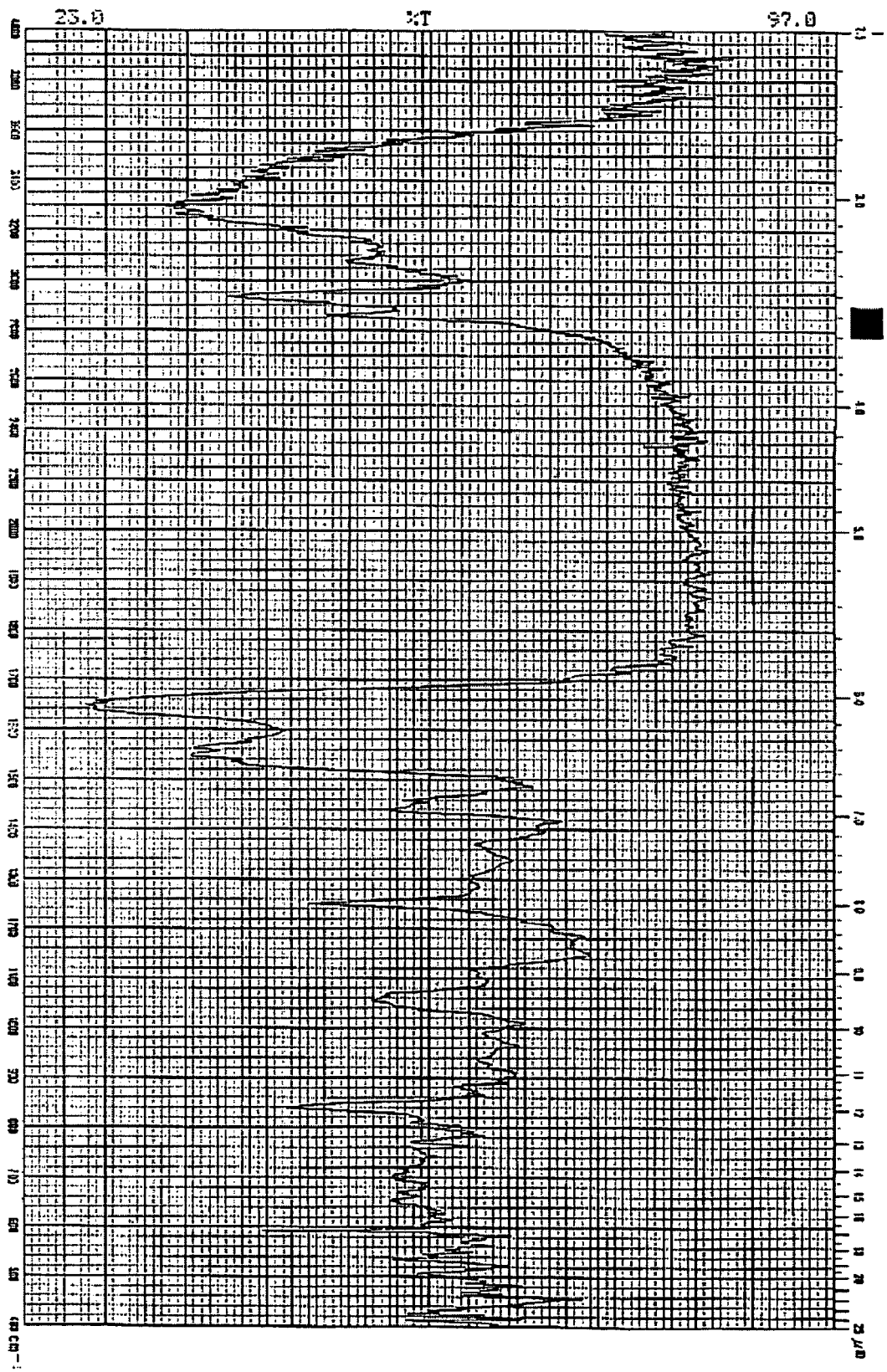
FIG. 7 shows an IR chart of an ε-polylysine used in the present invention.

After placing 2.00 g of ε-polylysine (number-average molecular weight=4090) and 20.0 g of methanol in a 100 milliliter three-necked flask equipped with a magnetic stirrer, condenser tube and thermometer, the mixture was stirred at room temperature for dissolution of the ε-polylysine. Next, 20.0 g of 2-propanol was added, the temperature was raised to 70° C., and then 9.14 g of the same polydimethylsiloxane used in Example 6, with a number-average molecular weight of 5000 and having an epoxy group at one end, was added dropwise over a period of 5 minutes. Reaction was conducted for 3 hours while maintaining a temperature of 70° C. The reaction mixture was cooled to room temperature, and then the volatile portion of the reaction mixture was distilled off under reduced pressure using an evaporator to obtain 11.0 g of the product, silicone-modified antimicrobial polymer (7) comprising silicone-modified ε-polylysine, as a faint yellow liquid. The structure of the product was confirmed by infrared absorption spectrum analysis (FIG. 6). The residual ratio of the number of amino groups of the polymer was 91%, and the silicone/ε-polylysine ratio was 80/20 (by weight).

2. Preparation of Silicone-modified Antimicrobial Agent Solutions

Example 8

The compound obtained in Example 1 was diluted with methanol to prepare a 10 wt % solution. Sterilized water was then used for further dilution to prepare test groups at 12.5 ppm, 25 ppm, 50 ppm, 100 ppm, 200 ppm, 400 ppm, 800 ppm and 1600 ppm.

Example 9

The compound obtained in Example 2 was diluted with methanol to prepare a 10 wt % solution. Sterilized water was then used for further dilution to prepare test groups at 12.5 ppm, 25 ppm, 50 ppm, 100 ppm, 200 ppm, 400 ppm, 800 ppm and 1600 ppm.

Example 10

The compound obtained in Example 3 was diluted with methanol to prepare a 10 wt % solution. Sterilized water was then used for further dilution to prepare test groups at 12.5 ppm, 25 ppm, 50 ppm, 100 ppm, 200 ppm, 400 ppm, 800 ppm and 1600 ppm.

Example 11

The compound obtained in Example 4 was diluted with ethanol to prepare a 10 wt % solution. Sterilized water was then used for further dilution to prepare test groups at 12.5 ppm, 25 ppm, 50 ppm, 100 ppm, 200 ppm, 400 ppm, 800 ppm and 1600 ppm.

Example 12

The compound obtained in Example 6 was diluted with methanol to prepare a 10 wt % solution. Sterilized water was then used for further dilution to prepare test groups at 12.5 ppm, 25 ppm, 50 ppm, 100 ppm, 200 ppm, 400 ppm, 800 ppm and 1600 ppm.

Example 13

The compound obtained in Example 7 was diluted with 2-propanol to prepare a 10 wt % solution. Sterilized water was then used for further dilution to prepare test groups at 12.5 ppm, 25 ppm, 50 ppm, 100 ppm, 200 ppm, 400 ppm, 800 ppm and 1600 ppm.

Reference Example 1

ε-Polylysine was diluted with sterilized water to prepare test groups at 12.5 ppm, 25 ppm, 50 ppm, 100 ppm, 200 ppm, 400 ppm, 800 ppm and 1600 ppm.

Reference Example 2

Methanol was diluted with sterilized water to prepare test groups at 112.5 ppm, 225 ppm, 450 ppm, 900 ppm, 1800 ppm, 3600 ppm, 7200 ppm and 14400 ppm.

Reference Example 3

Ethanol was diluted with sterilized water to prepare test groups at 112.5 ppm, 225 ppm, 450 ppm, 900 ppm, 1800 ppm, 3600 ppm, 7200 ppm and 14400 ppm.

Reference Example 4

2-Propanol was diluted with sterilized water to prepare test groups at 112.5 ppm, 225 ppm, 450 ppm, 900 ppm, 1800 ppm, 3600 ppm, 7200 ppm and 14400 ppm.

3. Antimicrobial Effects Against *E. coli*

The test groups of Examples 8-13 and Reference Examples 1-4 were used to measure antimicrobial effects against *Escherichia coli* IFO3972.

3-1. Medium Preparation

After dispensing 4.5 mL of nutrient broth medium (hereinafter, "NB medium") in a test tube and lightly closing the aluminum cap, it was subjected to autoclave sterilization for 15 minutes at 121° C., 1.1 kPa to obtain sterilized NB medium.

3-2. Antimicrobial Test

A 0.5 mL portion of each of the test groups of Examples 8-13 and Reference Examples 1-4 was added to the sterilized NB medium prepared under "3-1. Medium preparation", and each mixture was stirred to a uniform dispersion. Next, 0.1 mL of an *E. coli* suspension was inoculated into each test group to a starting cell number on the level of $10^5$ cells/mL, and then shake culturing was carried out for 48 hours in an incubator at 36° C. After completion of the culturing procedure, the bacterial growth inhibiting effect was judged by visual observation, based on whether or not the medium became turbid. The test results are shown in Tables 1 and 2. The groups exhibiting an antimicrobial effect were indicated by "G" while those which exhibited bacterial growth were indicated by "P".

TABLE 1

| Concentration (ppm) | 0 | 12.5 | 25 | 50 | 100 | 200 | 400 | 800 | 1600 |
|---|---|---|---|---|---|---|---|---|---|
| Example 8 | P | G | G | G | G | G | G | G | G |
| Example 9 | P | P | P | P | P | G | G | G | G |
| Example 10 | P | P | P | P | G | G | G | G | G |
| Example 11 | P | P | P | P | P | P | G | G | G |
| Example 12 | P | P | P | P | P | P | G | G | G |
| Example 13 | P | P | P | P | P | P | G | G | G |
| Reference Example 1 | P | P | P | G | G | G | G | G | G |

TABLE 2

| Concentration (ppm) | 0 | 112.5 | 225 | 450 | 900 | 1800 | 3600 | 7200 | 11400 |
|---|---|---|---|---|---|---|---|---|---|
| Reference Example 2 | P | P | P | P | P | P | P | P | P |
| Reference Example 3 | P | P | P | P | P | P | P | P | P |
| Reference Example 4 | P | P | P | P | P | P | P | P | P |

As clearly seen from Examples 8 to 13 in Table 1, the silicone-modified antimicrobial agents of the invention exhibited powerful antimicrobial effects against *E. coli*. Furthermore, the results for Reference Examples 2-4 in Table 2 demonstrated no influence on antimicrobial effect by the methanol, ethanol or 2-propanol mixed with the test groups.

4. Toxicity Test

The compound obtained in Example 4 was used for an acute oral toxicity test in rats at Safety Research Institute for Chemical Compounds Co., Ltd.

After suspending 5000 mg/kg of the compound obtained in Example 4 in a 0.5 wt % aqueous carmellose sodium solution, the toxicity thereof was examined by single dose administration to groups comprising five male and female Crj:CD(SD) IGS rats each. As a result, absolutely no abnormalities were found in the general conditions, body weight changes or examined findings among either the males or females, and no deaths occurred, during the 14 days after administration of 5000 mg/kg. On this basis it was concluded that the general lethal dose of the compound obtained in Example 4 was a dose exceeding 5000 mg/kg.

5. Solubility Test

The compounds obtained in Examples 1-7 were subjected to solubility tests in various solvents.

The compounds obtained in Examples 1-7 were added at 2 wt % to various organic solvents and subjected to an ultrasonic washer for 10 minutes, and the solubilities were visually confirmed. The results are shown in Table 3. Uniform solubility was indicated by "G", partial solubility was indicated by "F" and lack of solubility was indicated by "P".

ized with a mill and then further dried under reduced pressure for 6 hours at 80° C., 133 Pa to obtain acrylic copolymer (1) having a weight-average molecular weight of 40,000.

Example 14

There were dissolved 2.7 g of acrylic copolymer (1) and 0.3 g of silicone-modified antimicrobial agent (4) in a mix solution of 6.0 g of toluene and 6.0 g of methanol to prepare an antimicrobial resin composition for coating having a silicone-modified antimicrobial agent content of 10 wt % based on solid portion. This was then coated onto a glass plate (5×5 cm) with a spin coater (2000 rpm, spinning time: 10 sec), pre-dried at 80° C. for 10 minutes and then dried at 150° C. for 120 minutes to fabricate a glass plate coated with an antimicrobial resin composition of the invention.

Example 15

There were dissolved 2.88 g of acrylic copolymer (1) and 0.12 g of silicone-modified antimicrobial agent (4) in a mix solution of 6.0 g of toluene and 6.0 g of methanol to prepare an antimicrobial resin composition for coating having a silicone-modified antimicrobial agent content of 4 wt % based on solid portion. This was then coated onto a glass plate (5×5 cm) with a spin coater (2000 rpm, spinning time: 10 sec), pre-dried at 80° C. for 10 minutes and then dried at 150° C. for

TABLE 3

| Sample | Example 1 | Example 2 | Example 3 | Example 4 | Example 5 | Example 6 | Example 7 | ε-Poly-lysine |
|---|---|---|---|---|---|---|---|---|
| Water | G | F | F | F | P | P | P | G |
| Methanol | G | G | G | G | G | G | P | G |
| Ethanol | G | G | F | G | G | P | F | P |
| 2-Propanol | F | G | P | G | G | P | G | P |
| Toluene | P | G | P | G | G | G | G | P |
| Acetone | P | G | P | G | G | P | P | P |
| Tetrahydrofuran | P | G | F | G | G | G | G | P |

As clearly seen from Table 3, the solubilities of the compounds obtained in Examples 1-7 in various organic solvents were improved over the solubility of ε-polylysine, although with some differences depending on the silicone type and content.

Synthesis of Acrylic Resin

Synthesis Example 1

After charging 0.5 g of azobisisobutyronitrile, 20.0 g of methyl methacrylate, 5.0 g of butyl acrylate and 38.3 g of toluene into a 100 ml 4-necked flask equipped with a stirrer, reflux condenser, thermometer and nitrogen gas inlet tube, bubbling was performed with nitrogen gas for 30 seconds, reaction was conducted for 5 hours at 70° C. and the reaction system was cooled to room temperature to suspend polymerization. The reaction mixture was then added dropwise into 800 ml of methanol to precipitate the polymer, and after pre-drying the precipitated polymer at 80° C., it was pulver- 120 minutes to fabricate a glass plate coated with an antimicrobial resin composition of the invention.

Example 16

There were dissolved 1.765 g of acrylic copolymer (1) and 0.235 g of silicone-modified antimicrobial agent (1) in a mix solution of 4.0 g of toluene and 4.0 g of methanol to prepare an antimicrobial resin composition for coating having a silicone-modified antimicrobial agent content of 11.8 wt % based on solid portion. This was then coated onto a glass plate (5×5 cm) with a spin coater (2000 rpm, spinning time: 10 sec), pre-dried at 80° C. for 10 minutes and then dried at 150° C. for 120 minutes to fabricate a glass plate coated with an antimicrobial resin composition of the invention.

Example 17

There were dissolved 1.882 g of acrylic copolymer (1) and 0.118 g of silicone-modified antimicrobial agent (1) in a mix solution of 4.0 g of toluene and 4.0 g of methanol to prepare an antimicrobial resin composition for coating having a silicone-modified antimicrobial agent content of 5.9 wt % based on solid portion. This was then coated onto a glass plate (5×5 cm) with a spin coater (2000 rpm, spinning time: 10 sec), pre-dried at 80° C. for 10 minutes and then dried at 150° C. for 120 minutes to fabricate a glass plate coated with an antimicrobial resin composition of the invention.

Example 18

There were dissolved 1.952 g of acrylic copolymer (1) and 0.048 g of silicone-modified antimicrobial agent (1) in a mix solution of 4.0 g of toluene and 4.0 g of methanol to prepare an antimicrobial resin composition for coating having a silicone-modified antimicrobial agent content of 2.4 wt % based on solid portion. This was then coated onto a glass plate (5×5 cm) with a spin coater (2000 rpm, spinning time: 10 sec), pre-dried at 80° C. for 10 minutes and then dried at 150° C. for 120 minutes to fabricate a glass plate coated with an antimicrobial resin composition of the invention.

Example 19

There were dissolved 1.826 g of acrylic copolymer (1) and 0.174 g of silicone-modified antimicrobial agent (3) in a mix solution of 4.0 g of toluene and 4.0 g of methanol to prepare an antimicrobial resin composition for coating having a silicone-modified antimicrobial agent content of 8.7 wt % based on solid portion. This was then coated onto a glass plate (5×5 cm) with a spin coater (2000 rpm, spinning time: 10 sec), pre-dried at 80° C. for 10 minutes and then dried at 150° C. for 120 minutes to fabricate a glass plate coated with an antimicrobial resin composition of the invention.

Example 20

There were dissolved 1.913 g of acrylic copolymer (1) and 0.087 g of silicone-modified antimicrobial agent (3) in a mix solution of 4.0 g of toluene and 4.0 g of methanol to prepare an antimicrobial resin composition for coating having a silicone-modified antimicrobial agent content of 4.4 wt % based on solid portion. This was then coated onto a glass plate (5×5 cm) with a spin coater (2000 rpm, spinning time: 10 sec), pre-dried at 80° C. for 10 minutes and then dried at 150° C. for 120 minutes to fabricate a glass plate coated with an antimicrobial resin composition of the invention.

Example 21

There were dissolved 1.948 g of acrylic copolymer (1) and 0.052 g of silicone-modified antimicrobial agent (3) in a mix solution of 4.0 g of toluene and 4.0 g of methanol to prepare an antimicrobial resin composition for coating having a silicone-modified antimicrobial agent content of 2.6 wt % based on solid portion. This was then coated onto a glass plate (5×5 cm) with a spin coater (2000 rpm, spinning time: 10 sec), pre-dried at 80° C. for 10 minutes and then dried at 150° C. for 120 minutes to fabricate a glass plate coated with an antimicrobial resin composition of the invention.

Comparative Example 1

There was dissolved 3.0 g of acrylic copolymer (1) in a mix solution of 4.0 g of toluene and 4.0 g of methanol to prepare a resin composition for coating. This was then coated onto a glass plate (5×5 cm) with a spin coater (2000 rpm, spinning time: 10 sec), pre-dried at 80° C. for 10 minutes and then dried at 150° C. for 120 minutes to fabricate a glass plate coated with the resin.

(Antimicrobial Test)

An antimicrobial test was conducted as follows, according to the "Film Adhesion Method" established as an antimicrobial test method for synthetic resins in the "Antimicrobial Evaluation Test Methods for Silver and Other Inorganic Antimicrobial Agents (1995)" by the Japan Society of Silver and Other Inorganic Antimicrobial Agents.

The glass plates obtained in Examples 14-21 and Comparative Example 1 were used as the test samples.

Separately, nutrient broth medium was diluted 500-fold with sterilized purified water and adjusted to a pH of 7.0±0.2 as a "1/500 medium", and then *Escherichia coli* IFO3972 was added with a sterilized pipette to a viable cell count of $6.0 \times 10^5$ cells/ml in the medium to prepare a test bacterial culture.

Each test sample was placed in a sterilized dish and 0.5 mL of the test bacterial culture was inoculated onto the test surface and covered with a sterilization-treated polyethylene film, after which culturing was carried out for 24 hours at a temperature of 36±1 C.° and a relative humidity of 90% or more. Upon completion of culturing, the cells attached to each test piece and film were thoroughly washed off into a sterilized dish using sterilized water (10 mL), and the viable cell count in 1 mL of the washed off solution was measured by the standard agar medium method. After completion of the test, the change difference was calculated by the following formula and the results shown in Table 4.

Untreated Sample
A: Viable cell count immediately after inoculation
B: Viable cell count after culturing for prescribed time
Antimicrobial-treated Sample
C: Viable cell count after culturing for prescribed time $$\text{Change difference} = \log_{10}(B/A) - \log_{10}(C/A)$$

(Contact Angle Measurement)

A CA-X Contact Angle Meter by Kyowa Interface Science Co., Ltd. was used to measure the contact angle of water at room temperature on the coated film. The results are shown in Table 4.

TABLE 4

| | Silicone-modified antimicrobial agent | | Antimicrobial test | |
|---|---|---|---|---|
| | Type | Content (wt %) | Change difference | Contact angle (deg) |
| Example 14 | (4) | 10 | 7 | 96 |
| Example 15 | (4) | 4 | 7 | 94 |
| Example 16 | (1) | 11.8 | 7 | 92 |
| Example 17 | (1) | 5.9 | 7 | 90 |
| Example 18 | (1) | 2.4 | 7 | 85 |
| Example 19 | (3) | 8.7 | 7 | 98 |
| Example 20 | (3) | 4.4 | 7 | 95 |
| Example 21 | (3) | 2.6 | 7 | 95 |
| Comp. Ex. 1 | — | 0 | 0 | 74 |

The antimicrobial resin compositions of the invention in Examples 14-21 clearly exhibited high antimicrobial properties against *E. coli* compared to the resin of Comparative Example 1 containing no antimicrobial agent. The antimicrobial resin compositions of Examples 14-21 also clearly had higher contact angles than the resin of Comparative Example 1. The antimicrobial resin compositions of Examples 14-21 were therefore antimicrobial resin compositions exhibiting antimicrobial properties in combination with the water-repellent property of silicone.

The amino group-containing antimicrobial polymers of the invention comprising polyorganosiloxanes in the molecule are novel compounds exhibiting both the properties of silicone, and antimicrobial properties. The amino group-containing antimicrobial agents used for the invention are naturally-derived and therefore highly safe for the human body. Moreover, the presence of siloxane groups in the molecule affords high solubility in organic solvents. The agents are therefore easily miscible with various resins, thereby facilitating preparation of antimicrobial resin compositions of the invention comprising the antimicrobial agents of the invention. The antimicrobial agents and antimicrobial resin compositions of the invention are expected to have practical applications in cosmetics, pharmaceuticals, dishwashing detergents, clothing detergents, fabric softeners, fabric finishers, adhesives, paints, inks, toys, paper products, fiber products, various synthetic resin molded articles, films, sheets, sterilizing sprays, wet tissues, wipers, waxes and the like.

What is claimed is:

1. ε-Polylysine represented by the following formula (1), having a polyorganosiloxane group introduced into the molecule (a polymer hereinafter referred to as "silicone-modified ε-polylysine")

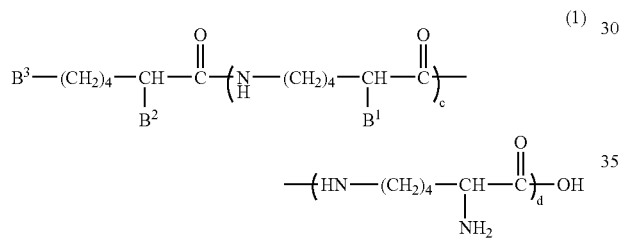

wherein $B^1$, $B^2$ and $B^3$ are groups represented by general formula (2) below or amino groups, and at least one thereof is a group represented by formula (2), c is an integer of 0 to 50, d is an integer of 0 to 50, and c+d is an integer of 1 to 50

—D—Y—Q  (2)

wherein D is a group represented by:

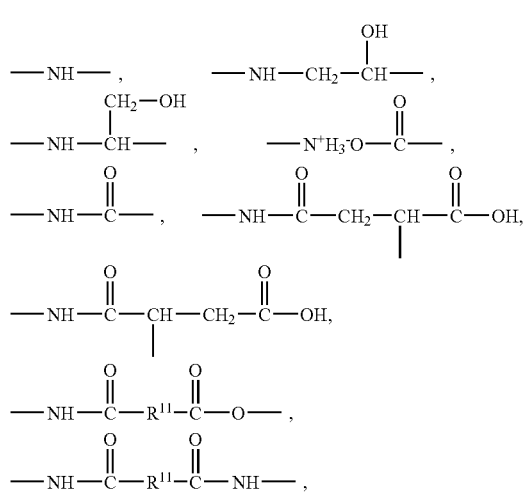

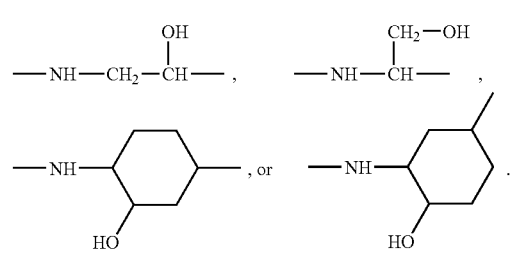

(wherein $R^{11}$ is C1-5 linear or branched alkylene, C2-5 alkenylene or C6-10 arylene), and Y is C1-1000 linear or branched alkylene, of which any mutually non-adjacent methylenes may be substituted with —O—, and Q is a polyorganosiloxane group represented by the following formula (3):

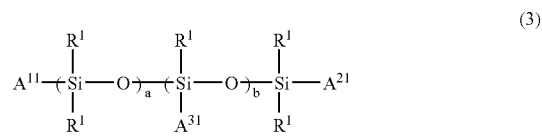

wherein each $R^1$ is independently C1-20 alkyl or C6-10 aryl, a is an integer of 0 to 1000, b is an integer of 0 to 1000, a+b is an integer of 1 to 1000, and $A^{11}$, $A^{21}$ and $A^{31}$ are independently $R^1$, or a monovalent residue which is a compound represented by formula (1) with Q removed, with one thereof being said monovalent residue.

2. Silicone-modified ε-polylysine according to claim 1, wherein D in formula (2) is one of the following groups 3. Silicone-modified ε-polylysine according to claim 1, wherein D in formula (2) is one of the following groups

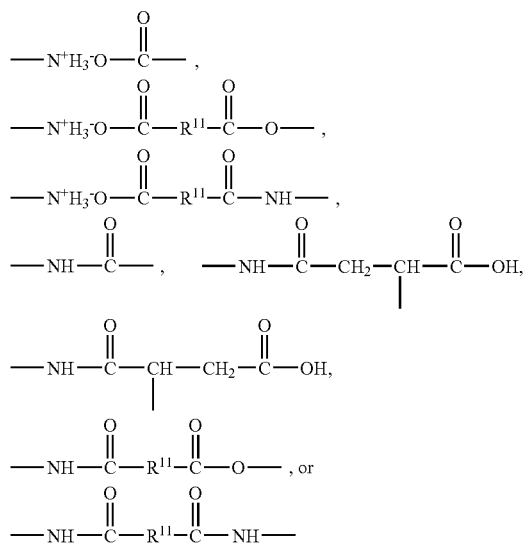

wherein $R^{11}$ is C1-5 linear or branched alkylene, C2-5 alkenylene or C6-10 arylene.

4. Silicone-modified ε-polylysine according to claim 1, wherein D in formula (2) is one of the following groups

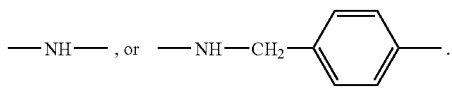

5. Silicone-modified ε-polylysine according to claim 1, wherein D in formula (2) is one of the following groups

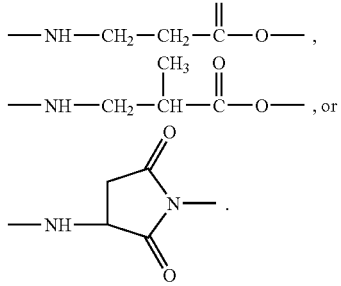

* * * * *